United States Patent
Gray et al.

(10) Patent No.: US 11,744,591 B2
(45) Date of Patent: Sep. 5, 2023

(54) MEDICAL DEVICE FOR ANASTOMOSIS

(71) Applicant: Xeltis, B.V., Eindhoven (NL)

(72) Inventors: Yonatan Gray, Eindhoven (NL); Mohammed El-Kurdi, Mansfield, MA (US)

(73) Assignee: Xeltis AG, Zurich (CH)

( * ) Notice: Subject to any disclaimer, the term of this patent is extended or adjusted under 35 U.S.C. 154(b) by 242 days.

(21) Appl. No.: 17/183,508

(22) Filed: Feb. 24, 2021

(65) Prior Publication Data

US 2021/0267599 A1 Sep. 2, 2021

Related U.S. Application Data

(60) Provisional application No. 62/982,161, filed on Feb. 27, 2020.

(51) Int. Cl.
| | | |
|---|---|---|
| *A61B 17/11* | (2006.01) | |
| *A61F 2/07* | (2013.01) | |
| *A61F 2/06* | (2013.01) | |
| *A61B 17/00* | (2006.01) | |

(52) U.S. Cl.
CPC ....... *A61B 17/11* (2013.01); *A61B 2017/1107* (2013.01); *A61B 2017/1132* (2013.01)

(58) Field of Classification Search
CPC . A61B 17/11; A61B 17/1114; A61B 17/1128; A61B 2017/1103; A61B 2017/1107; A61B 2017/1121; A61B 2017/1132; A61B 2017/1135;
(Continued)

(56) References Cited

U.S. PATENT DOCUMENTS

| | | |
|---|---|---|
| 5,151,105 A | 9/1992 | Kwan-Gett |
| 5,851,232 A * | 12/1998 | Lois ............. A61F 2/2412 623/1.13 |
| 6,743,243 B1 | 6/2004 | Roy |

(Continued)

FOREIGN PATENT DOCUMENTS

| | | |
|---|---|---|
| CN | 108652788 | 10/2018 |
| WO | WO1999045852 | 9/1999 |

(Continued)

*Primary Examiner* — Katherine M Shi
*Assistant Examiner* — Lindsey R. Rivers
(74) *Attorney, Agent, or Firm* — LUMEN PATENT FIRM

(57) ABSTRACT

A medical device for an anastomosis is provided. The medical device distinguishes an inner tubular layer, an outer tubular layer, and a support element defining a longitudinal axis. It further distinguishes two or more independent C-rings distributed and positioned at an acute orientation angle relative to the longitudinal axis of the support element at one end of the support element. The support element and the two or more C-rings are embedded in between the inner and the outer tubular layers. The types of applications one could envision are e.g. a proximal anastomosis, distal anastomosis, or side-to-side anastomoses, in a customized prefabricated graft. Embodiments of the invention could also be incorporated into an anastomotic connector device design. Embodiments of the invention could further be envisioned as vascular grafts applications such as Coronary Artery Bypass Graft (CABG), dialysis access grafts and peripheral vascular applications.

13 Claims, 5 Drawing Sheets

(58) Field of Classification Search
CPC .... A61B 2017/1139; A61F 2/064; A61F 2/82; A61F 2/86; A61F 2/88; A61F 2/885; A61F 2/89
See application file for complete search history.

(56) References Cited

U.S. PATENT DOCUMENTS

| | | | |
|---|---|---|---|
| 6,808,533 B1* | 10/2004 | Goodwin | A61F 2/86 623/1.13 |
| 8,083,790 B2 | 12/2011 | Lentz | |
| 9,254,208 B2 | 2/2016 | Ischinger | |
| 9,409,002 B2 | 8/2016 | Shelton | |
| 10,285,702 B2 | 5/2019 | Jose | |
| 10,449,026 B2 | 10/2019 | Sostek | |
| 2002/0099392 A1 | 7/2002 | Mowry | |
| 2004/0193246 A1* | 9/2004 | Ferrera | A61F 2/954 623/1.15 |
| 2010/0094327 A1* | 4/2010 | Milsom | A61B 17/0218 606/191 |
| 2011/0230955 A1* | 9/2011 | Orion | A61F 2/064 623/1.15 |
| 2011/0288628 A1* | 11/2011 | Noesner | B29C 66/729 156/195 |
| 2014/0141152 A1* | 5/2014 | Sostek | D04H 1/43835 427/2.24 |

FOREIGN PATENT DOCUMENTS

| | | |
|---|---|---|
| WO | WO2000027305 | 5/2005 |
| WO | WO2011084559 | 7/2011 |

\* cited by examiner

MEDICAL DEVICE FOR ANASTOMOSIS

CROSS-REFERENCE TO RELATED APPLICATIONS

This application claims priority from U.S. Provisional Patent Application 62/982,161 filed Feb. 27, 2020, which is incorporated herein by reference.

FIELD OF THE INVENTION

This invention relates to medical devices. In particular, the invention relates to a medical device for anastomosis

BACKGROUND OF THE INVENTION

Coronary artery bypass graft (CABG) surgery is a surgical procedure to restore blood flow to an obstructed coronary artery. When considering a CABG proximal anastomosis, the proximal portion of the graft is required to be trimmed at nominally about a 45 degree-angle and sutured to a punched hole in the aorta. If a pure polymer tube is sewn at the proximal anastomosis there is the concern of toe flattening, and/or heel buckling/ovalization/kinking. If an incorporated support element (e.g. a Strain Relief System (SRS)) is used as part of the anastomosis the support element has to be trimmed and this leads to "toe flattening" creating a compromised flow pattern at the inlet. Additionally, metallic struts that are being incorporated in the anastomosis potentially create a risk of irritation by sharp edges, or migration of fragments, which could result in side effects such as inflammatory response or intimal hyperplasia. Other metallic support element structures utilized for CABG devices such as braided or knitted meshes could easily unravel when trimmed to be incorporated into the anastomosis. Accordingly, there is a need in the art to design a new structure that would overcome at least some of these concerns or problems.

SUMMARY OF THE INVENTION

The present invention provides a medical device for an anastomosis. The medical device distinguishes an inner tubular layer, an outer tubular layer, and a support element defining a longitudinal axis. It further distinguishes two or more independent C-rings distributed and positioned at an acute orientation angle relative to the longitudinal axis of the support element at one end of the support element. The support element and the two or more C-rings are embedded in between the inner and the outer tubular layers.

In one aspect of the invention, the support element could further have an end-ring attached to the one end of the support element. The end-ring is aligned more or less in parallel, adjacent, yet independent to the two or more C-rings.

In another aspect of the invention, the inner tubular layer and/or outer tubular layer are an electrospun layer.

In yet another aspect of the invention, the two or more C-rings are circular or oval.

In yet another aspect of the invention, the two or more C-rings are closed C-rings.

In yet another aspect of the invention, the end-ring is an oval closed end-ring, an oval open end-ring, a circular closed end-ring or a circular open end-ring.

In yet another aspect of the invention, the two or more C-rings are made of nitinol.

In yet another aspect of the invention, the distance between the end-ring attached to the support element and the first independent C-ring is nominally in the range of 0.5 to 1.5 mm.

In yet another aspect of the invention, the distance in between two adjacent C-rings in the two or more independent C-rings is nominally in the range of 1.5 to 2.5 mm.

In yet another aspect of the invention, the two or more C-rings are under pre-load.

In yet another aspect of the invention, the acute orientation angle is a 30-60 degree-angle or a 15-90 degree-angle.

In still another aspect of the invention, the support element is a stent, an SRS, a coil, a wire, a braid or any other type of support structure used in cardiovascular implants.

Embodiments of the invention have at least the following advantages.

- The independent rings enable a surgeon with a trimmable a desired trimming length at the proximal and/or distal end.
- Cutting between the rings will avoid cutting through metal.
- The shape of the rings and the pitch between two adjacent rings enables good kink resistance near an anastomosis.
- The opening of each independent ring allows a surgeon to cut the graft axially to enlarge the area of the anastomosis (i.e. create a "Cobra-head") for optimal flow through the anastomosis and reduction of intimal hyperplasia as well as better accommodation of intimal hyperplasia, if it occurs.
- The independent ring being sutured to the anastomosis can and will expand gradually in the radial direction reactive to the arterial pressure. This will help reduce excessive shear stress at the anastomosis (and reduction of intimal hyperplasia).
- Due to the rigid circular/oval shape of the ring and the rigidity of the metal at the toe of an anastomosis, buckling of the polymer is prevented and toe flattening is reduced.
- The c-rings, by virtue of their ability to open radially, enable a larger graft ostium diameter than the inner diameter of the main body of the graft, thus creating a funneling effect which optimizes blood flow for optimal chronic patency (at the anastomosis).
- The number of rings used could be increased (using a modular production tool-see 400 in FIGS. 4-5) to allow a longer trimmable section if needed.
- An array of independent rings has sufficient kink resistance for numerous applications of anastomoses in bypassing small diameter vessels.

DETAILED DESCRIPTION

Figure 1:
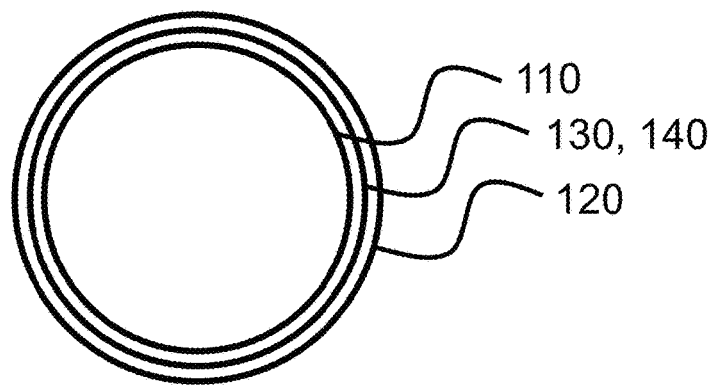
FIG. 1 shows according to an exemplary embodiment of the invention a medical device with two tubular layers (inner layer 110, outer layer 120) that embed a support element 130 and two or more independent C-rings 140 (cross-sectional view).
Figure 2:
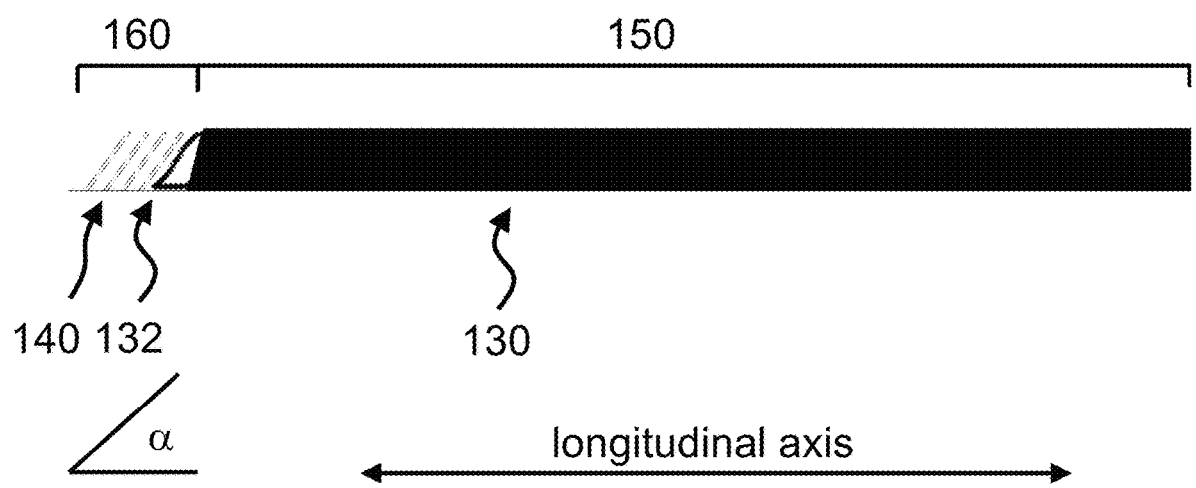
FIGS. 2-3 show according to an exemplary embodiment of the invention a medical device with a support element 130 with an end-ring 132 attached to the support element 130. This support element end-ring 132 is aligned more or less in parallel to the two or more independent C-rings 140.
Figure 3:
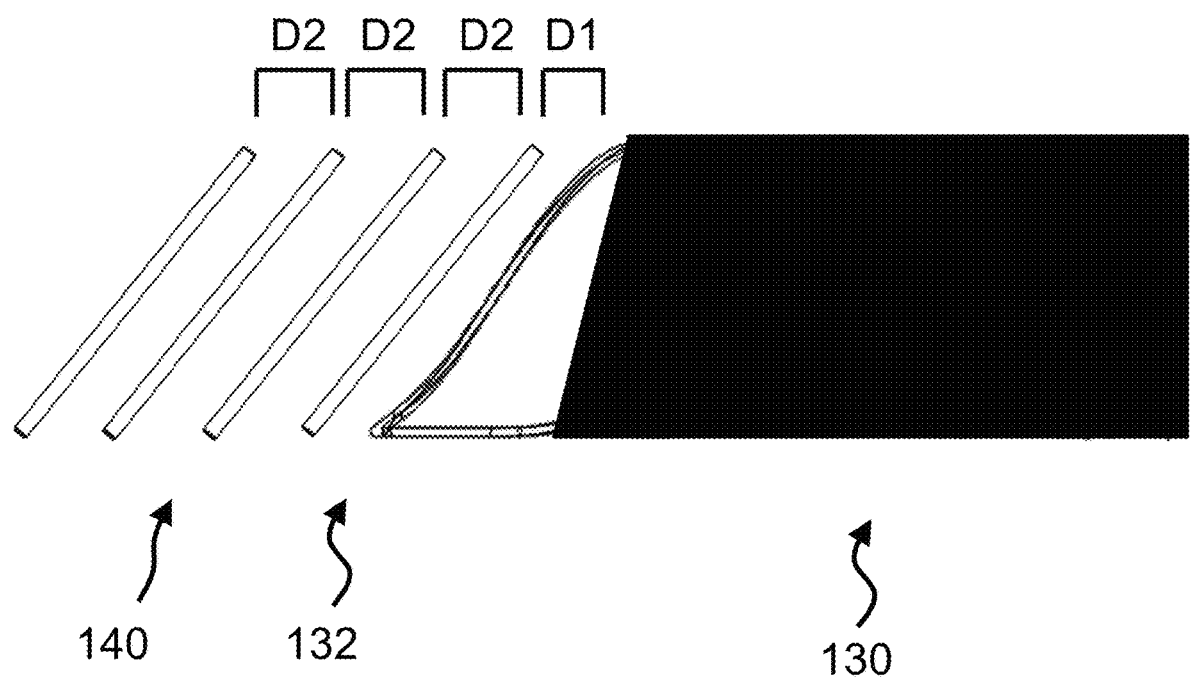
Figure 4:
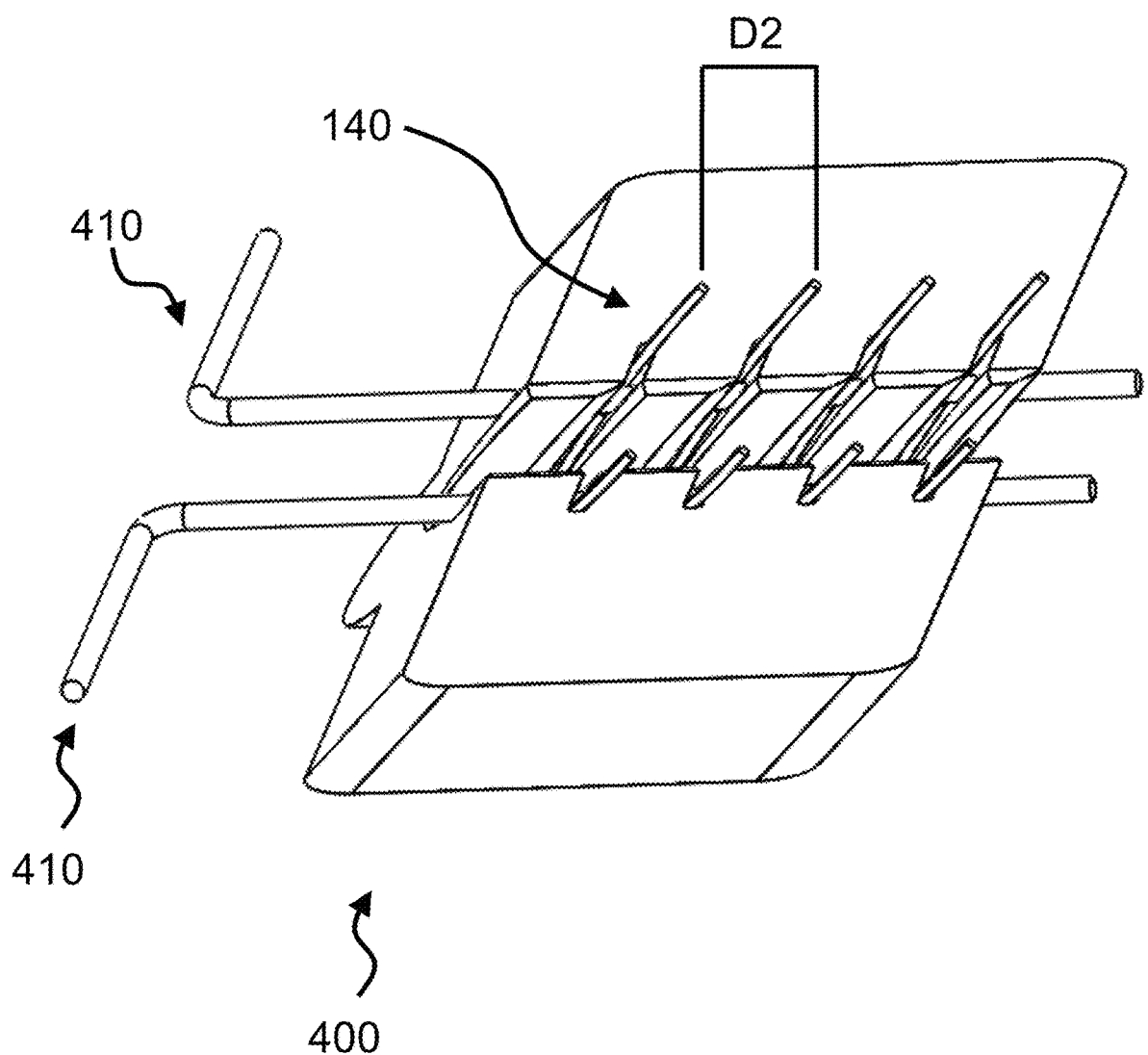
FIGS. 4-5 show according to an exemplary embodiment of the invention a tool which can assist in positioning the C-rings as well as controlling the spacing of the C-rings relative to the implant. Rings are over expanded using spacing wires 410. Upon removal of wires, C-rings deployed to final position.
Figure 5:
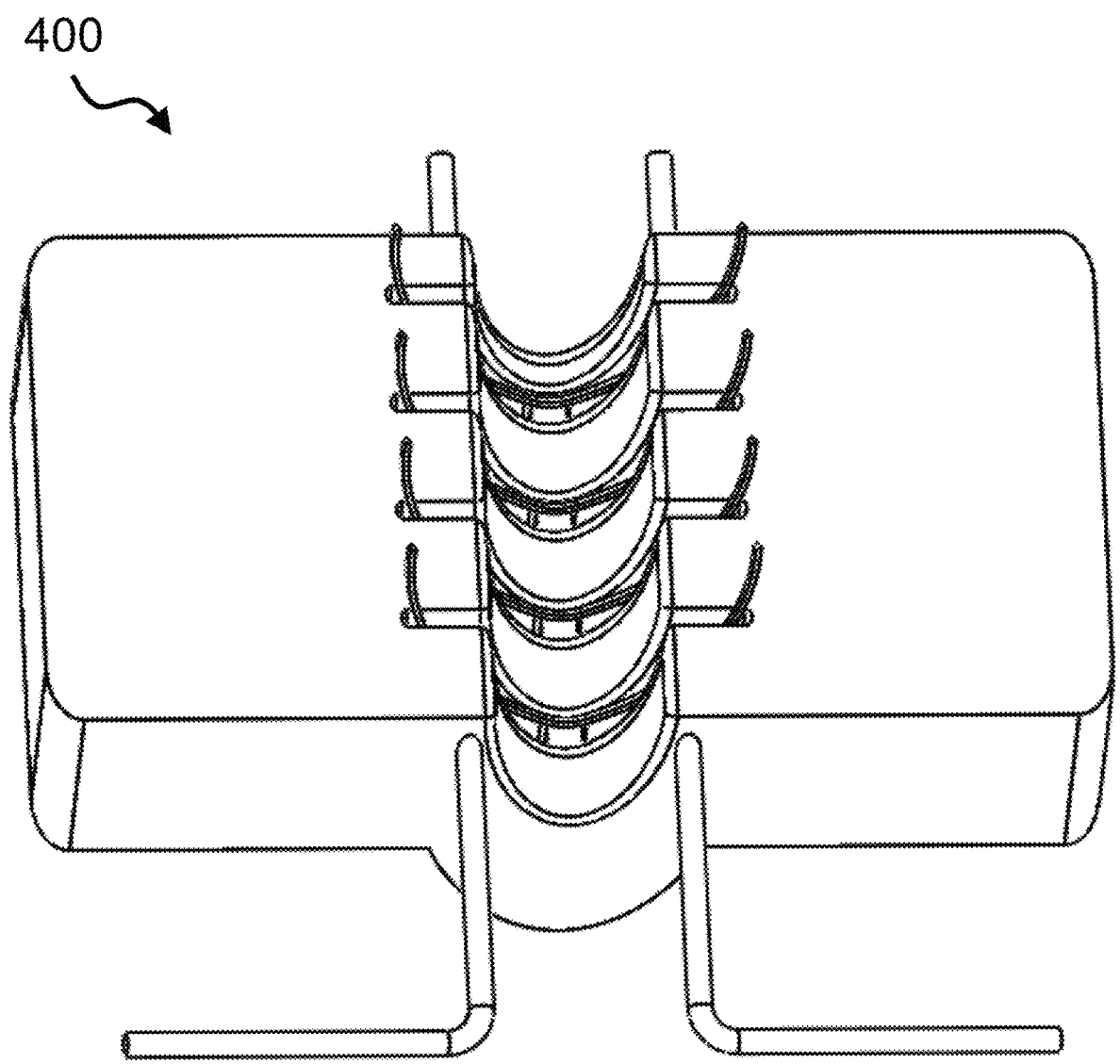

The present invention is a medical device incorporating a support element for the purposes of anastomosis. Examples of such a support element are a stent, an SRS, a coil, a wire, braid or any other type of support structure typically used in cardiovascular implants. The medical device has two tubular layers (inner layer 110, outer layer 120) that embed the support element 130 as well as two or more independent (separate) C-rings 140 near the end of the support element. A C-ring is defined as either a circular or oval ring that is not fully closed; i.e. has an opening, large enough to accommodate standard surgical scissors for axial slit creation without cutting through the ring strut. In one embodiment, the openings of the C-rings of the two or more independent C-rings are aligned with each other (see FIGS. 2-5). In an alternate embodiment, the C-rings could be closed rings.

Defining a longitudinal axis of the medical device, the medical device then distinguishes a (main) body section/part 150 where the support element is positioned and a proximal end section/part 160 adjacent to one end of the body section/part where two or more independent C-rings 140 are distributed and positioned at an acute orientation angle relative to the longitudinal axis. Depending on the application the of acute orientation angle could be a 15-90 degree-angle or preferably a 30-60 degree-angle, or nominally a 45 degree-angle.

The C-rings are embedded in between the inner and outer tubular layers, in a way that prevents delamination of the layers. In one embodiment, the orientation angle is nominally about 45 degrees, which coincides with the typical angle used by a surgeon to cut and trim the medical device for an anastomosis procedure. In other words, the surgeon will cut the medical device in between two C-rings (i.e. the trimmable tip), as the most outer C-ring is preferably incorporated into the anastomosis. That is, if the suture is placed around the C-ring, then by controlling the spacing between the adjacent c-rings, it is possible to eliminate/minimize toe flattening and/or heel buckling of the graft anastomoses.

In one embodiment, the support element 130 has an oval or circular end-ring 132 attached to (and part of) the support element. This so-called end-ring 132 is aligned more or less in parallel to the two or more independent C-rings 140.

In a preferred embodiment, the inner and outer tubular layer are electrospun layers and the two or more oval c-rings are made of nitinol.

The distance D1 between the end-ring of the main body of the support element and the first C-ring is in the range of 0.5 mm to 1.5 mm, or 0.5 mm to 2 mm, and preferably about 1 mm. These exemplary spacings are a function of diameter and in these examples work well for a 4 mm inner-diameter graft. For larger diameter grafts (i.e. a thoracic graft), they could be up to 5 mm.

The distance D2 in between two adjacent C-rings in the two or more C-rings is in the range of 1.5 mm to 2.5 mm or 1.5 mm to 3 mm, and preferably about 2 mm. Likewise for D2 as for D1 for larger implants this spacing would be larger.

Application dependent, but for a design it would be fair to consider that D1 is always smaller than D2 as it might be necessary to prevent the first free ring from tucking up inside the fixed ring.

Figure 6:
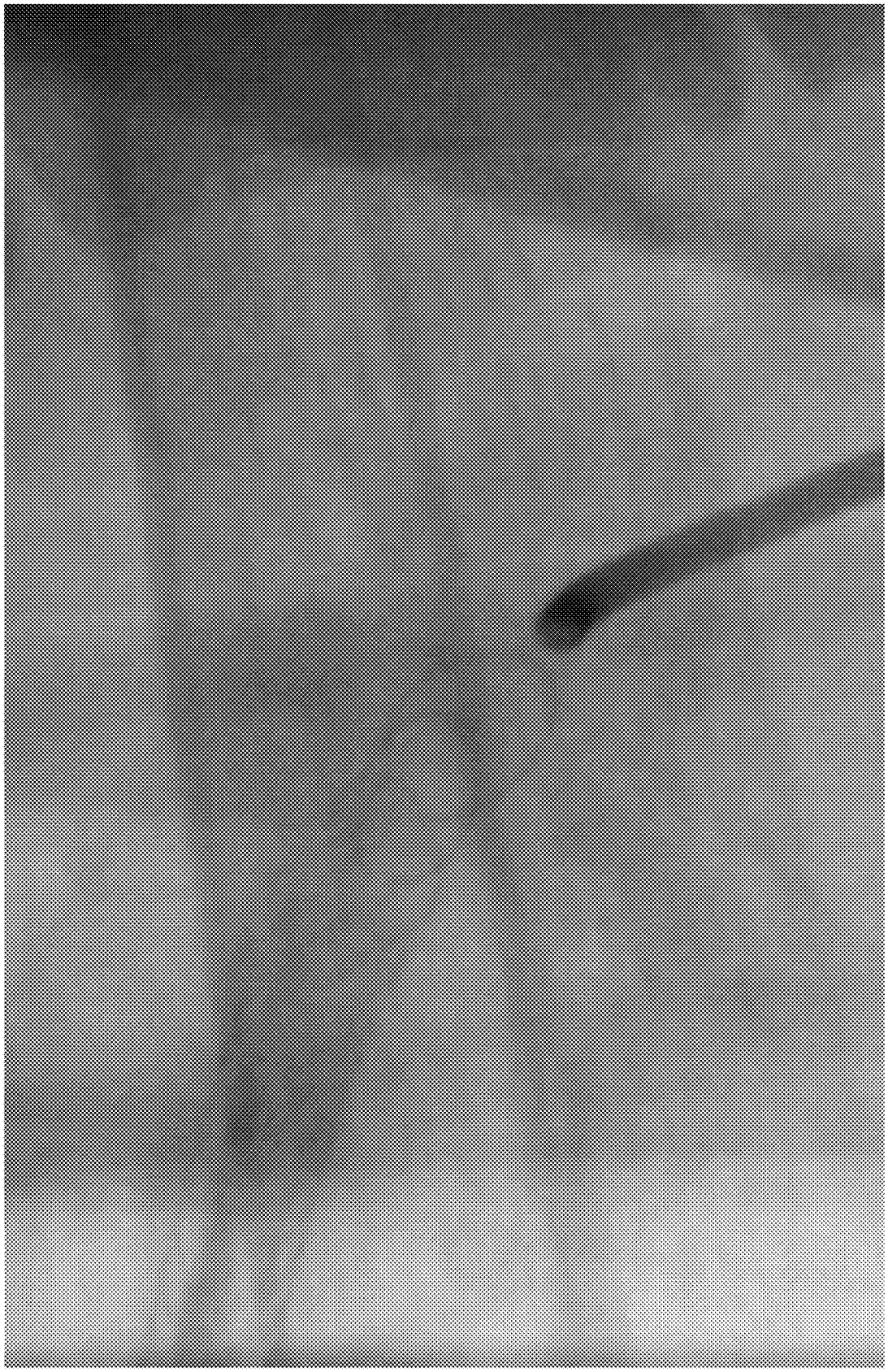
FIG. 6 shows an angiogram according to an embodiment of the invention with C-rings incorporated in an anastomosis.

In an exemplary embodiment, by design, the C-rings allow a projection of about 45 degrees when assembled on for example a 4.5 mm diameter inner tubular layer. Therefore, when one considers an assembly on a 4.7 mm inner tubular layer, this will result in the C-rings to have a "pre-load" due to the inner tubular layer pushing back on them. It is also noted that the C-ring structure maintains its function, i.e. not kinking due to graft bending curvature, as long as the adjacent support element has at its proximal end incorporated a ring of very similar orientation and similar geometry (e.g. strut width, thickness). The C-ring structure allows for radial expansion to conform to the size of the aortotomy, which ideally results in a funnel shape at the inlet of the graft, thereby improving hemodynamics. This phenomenon was repeatedly observed in-vivo during chronic animal study follow-up via angiograms (FIG. 6)

The fact that the end has independently spaced C-rings only, and no wires, the surgeon will not have to cut through the wires. Furthermore, the C-ring geometry eliminates 'toe flattening' and heel buckling at the anastomosis because a ring-based support element can effectively prevent radial deformation.

The C-rings can be laser cut from a metallic tube or flat sheet, preferably from Nitinol. The contour of the C-ring should avoid sharp edges that may cause long-term abrasion with surrounding tissue and therefore should be smoothened (e.g. mechanically or electrically polished). The opening of the C-ring should be wide enough to allow the end user to cut a slit axially through the ring as a common vascular surgery technique without actually cutting the C-ring.

The medical device could be made by a process where an inner tubular layer 110 is electro-spun on a metal rod (not shown). The support element 130 could then be laid over the inner tubular electro-spun layer 110. C-rings 140 could then be deployed on top of inner layer 110 in a controlled position to ensure accurate distance and orientation to the edge of the main body 150 of implant 130. Preferably for the deployment of the C-rings, a dedicated tool 400 could be used (see FIGS. 4-5). Tool 400 should allow widening of the C-rings 140 contour beyond tubular layer circumference and a steady release of rings to its final location, being tight against tubular inner layer. Arms 410 could be integrated with tool 400 to control the opening of the C-rings 140. Finally, a tubular outer layer 120 is electro-spun to cover the support element 130 and the C-rings 140 to provide a smooth connectivity of electro-spun fibres of inner and outer layers to form a single electro spun tubular assembly.

The electrospun material referenced in this document may comprise the ureido-pyrimidinone (UPy) quadruple hydrogen-bonding motif (pioneered by Sijbesma (1997), Science 278, 1601-1604) and a polymer backbone, for example selected from the group of biodegradable polyesters, polyurethanes, polycarbonates, poly(orthoesters), polyphosphoesters, polyanhydrides, polyphosphazenes, polyhydroxalkanoates, polyvinylalcohol, polypropylenefumarate. Examples of polyesters are polycaprolactone, poly(L-lactide), poly(DL-lactide), poly(valerolactone), polyglycolide, polydioxanone, and their copolyesters. Examples of polycarbonates are poly(trimethylenecarbonate), poly(dimethyl-trimethylenecarbonate), poly(hexamethylene carbonate).

The same result may be obtained with alternative, non-supramolecular polymers, if properties are carefully selected and material processed to ensure required surface characteristics. These polymers may comprise biodegradable or non-biodegradable polyesters, polyurethanes, polycarbonates, poly(orthoesters), polyphosphoesters, polyanhydrides, polyphosphazenes, polyhydroxyalkanoates, polyvinylalcohol, polypropylenefumarate. Examples of polyesters are polycaprolactone, poly(L-lactide), poly(DL-lactide), poly(valerolactone), polyglycolide, polydioxanone, and their copolyesters. Examples of polycarbonates are poly(trimethylenecarbonate), poly(dimethyltrimethylenecarbonate), poly(hexamethylene carbonate).

Examples of Applications

The types of applications one could envision are e.g. a proximal anastomosis, distal anastomosis, or side-to-side anastomoses, in a customized pre-fabricated graft. Embodiments of the invention could also be incorporated into an anastomotic connector device design. Embodiments of the invention could further be envisioned as (small caliber) vascular grafts applications such as CABG, dialysis access grafts and peripheral vascular applications, including, but not limited to, critical limb ischemia, Fem-Pop grafts, or BTK grafts.

What is claimed is:

1. A medical device for an anastomosis, comprising:
   (a) an inner tubular layer;
   (b) an outer tubular layer;
   (c) a support element defining a longitudinal axis; and
   (d) two or more independent C-rings distributed and positioned at an acute orientation angle relative to the longitudinal axis of the support element at one end of the support element,
   wherein the support element and the two or more C-rings are embedded in between the inner and the outer tubular layers,
   wherein the support element further comprises an end-ring attached to the one end of the support element, wherein the end-ring is aligned substantially in parallel, adjacent, yet independent to the two or more C-rings.

2. The medical device as set forth in claim 1, wherein the inner tubular layer is an electrospun layer.

3. The medical device as set forth in claim 1, wherein the outer tubular layer is an electrospun layer.

4. The medical device as set forth in claim 1, wherein the two or more C-rings are circular or oval.

5. The medical device as set forth in claim 1, wherein the two or more C-rings are closed.

6. The medical device as set forth in claim 1, wherein the end-ring is an oval closed end-ring, an oval open end-ring, a circular closed end-ring or a circular open end-ring.

7. The medical device as set forth in claim 1, wherein the two or more C-rings are made of nitinol.

8. The medical device as set forth in claim 1, wherein a distance between the end-ring attached to the support element and the first independent C-ring is in the range of 0.5 to 1.5 mm.

9. The medical device as set forth in claim 1, wherein a distance in-between two adjacent C-rings in the two or more independent C-rings is in the range of 1.5 to 2.5 mm.

10. The medical device as set forth in claim 1, wherein the acute orientation angle is a 30 degree angle to a 60 degree angle.

11. The medical device as set forth in claim 1, wherein the acute orientation angle is a 15 degree angle to a 90 degree angle.

12. The medical device as set forth in claim 1, wherein the support element is a stent, an SRS, a coil, a wire, a braid or any other type of support structure used in cardiovascular implants.

13. The medical device as set forth in claim 1, wherein the two or more C-rings are under pre-load.

* * * * *